US010258770B2

United States Patent
Wang et al.

(10) Patent No.: US 10,258,770 B2
(45) Date of Patent: Apr. 16, 2019

(54) SUBINTIMAL RE-ENTRY CATHETER WITH SHAPE CONTROLLED BALLOON

(71) Applicant: Boston Scientific Scimed, Inc., Maple Grove, MN (US)

(72) Inventors: Huisun Wang, Maple Grove, MN (US); Pu Zhou, Trabuco Canyon, CA (US); Benjamin Gundale, Plymouth, MN (US); Daniel Horn, Shoreview, MN (US); John Chen, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 614 days.

(21) Appl. No.: 14/204,130

(22) Filed: Mar. 11, 2014

(65) Prior Publication Data

US 2014/0277053 A1 Sep. 18, 2014

Related U.S. Application Data

(60) Provisional application No. 61/781,150, filed on Mar. 14, 2013.

(51) Int. Cl.
*A61M 25/01* (2006.01)
*A61B 17/3207* (2006.01)
(Continued)

(52) U.S. Cl.
CPC ..... *A61M 25/0194* (2013.01); *A61B 17/3207* (2013.01); *A61M 25/1002* (2013.01);
(Continued)

(58) Field of Classification Search
CPC .......... A61M 25/0194; A61M 25/1002; A61M 25/104; A61M 2025/0197;
(Continued)

(56) References Cited

U.S. PATENT DOCUMENTS 5,304,214 A * 4/1994 DeFord ................ A61B 18/082
604/916
5,830,181 A * 11/1998 Thornton ............ A61M 25/104
604/102.01

(Continued)

FOREIGN PATENT DOCUMENTS

| EP | 2886151 A1 * | 6/2015 | ........ A61M 25/1034 |
|---|---|---|---|
| WO | 2009100129 A2 | 8/2009 | |
| WO | 2013003194 A1 | 1/2013 | |

*Primary Examiner* — David C Eastwood
(74) *Attorney, Agent, or Firm* — Seager, Tufte & Wickhem LLP

(57) ABSTRACT

A recanalization catheter for facilitating re-entry into a lumen of a blood vessel from a subintimal space. The catheter includes an inflatable balloon mounted on a distal end region of the catheter shaft of the catheter. The catheter shaft includes a guidewire lumen having a distal opening and a lateral opening in a distal region of the catheter shaft proximal of the distal opening, and an inflation lumen in fluid communication with the balloon. The balloon is configured to be inflated in the subintimal space to a first inflation state at inflation pressures below a threshold inflation pressure to orient the lateral opening toward the lumen of the blood vessel, and inflated to a second inflation state at inflation pressures above the threshold inflation pressure. The catheter includes means for retaining the balloon in the first inflation state at pressures below the threshold inflation pressure.

19 Claims, 13 Drawing Sheets

(51) Int. Cl.
*A61M 25/10* (2013.01)
*A61B 17/22* (2006.01)
*A61M 25/00* (2006.01)

(52) U.S. Cl.
CPC .............. *A61B 2017/22044* (2013.01); *A61B 2017/22068* (2013.01); *A61B 2017/22071* (2013.01); *A61B 2017/22095* (2013.01); *A61M 25/104* (2013.01); *A61M 2025/0095* (2013.01); *A61M 2025/0197* (2013.01); *A61M 2025/1059* (2013.01); *A61M 2025/1084* (2013.01)

(58) Field of Classification Search
CPC .. A61M 2025/1059; A61M 2025/0095; A61M 2025/1072; A61M 2025/1068; A61M 2025/105984; A61M 2025/1004; A61M 25/1009; A61M 2025/1043; A61M 2025/1047; A61M 2025/1054; A61B 17/3207; A61B 2017/22068; A61B 2017/22044; A61B 2017/22071; A61B 2017/22095
USPC .......................... 604/103.06, 7; 606/192, 194
See application file for complete search history.

(56) References Cited

U.S. PATENT DOCUMENTS

| | | | |
|---|---|---|---|
| 5,830,222 A | 11/1998 | Makower | |
| 5,935,108 A | 8/1999 | Katoh et al. | |
| 5,938,671 A | 8/1999 | Katoh et al. | |
| 5,951,513 A * | 9/1999 | Miraki | A61M 25/1027 604/96.01 |
| 5,968,064 A | 10/1999 | Selmon et al. | |
| 5,976,181 A * | 11/1999 | Whelan | A61F 2/958 606/194 |
| 6,010,449 A | 1/2000 | Selmon et al. | |
| 6,068,638 A | 5/2000 | Makower | |
| 6,120,516 A | 9/2000 | Selmon et al. | |
| 6,159,225 A | 12/2000 | Makower | |
| 6,190,353 B1 | 2/2001 | Makower et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,398,798 B2 | 6/2002 | Selmon et al. | |
| 6,506,178 B1 | 1/2003 | Schubart et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,579,302 B2 | 6/2003 | Duerig et al. | |
| 6,599,304 B1 | 7/2003 | Selmon et al. | |
| 6,638,247 B1 | 10/2003 | Selmon et al. | |
| 6,663,577 B2 | 12/2003 | Jen et al. | |
| 6,709,444 B1 | 3/2004 | Makower | |
| 6,719,725 B2 | 4/2004 | Milo et al. | |
| 6,955,175 B2 | 10/2005 | Stevens et al. | |
| 7,004,173 B2 | 2/2006 | Sparks et al. | |
| 7,179,270 B2 | 2/2007 | Makower | |
| 7,229,421 B2 | 6/2007 | Jen et al. | |
| 7,357,794 B2 | 4/2008 | Makower et al. | |
| 7,740,623 B2 | 6/2010 | Nayak et al. | |
| 7,918,859 B2 | 4/2011 | Katoh et al. | |
| 7,918,870 B2 | 4/2011 | Kugler et al. | |
| 7,938,819 B2 | 5/2011 | Kugler et al. | |
| 8,025,655 B2 | 9/2011 | Kugler et al. | |
| 8,083,727 B2 | 12/2011 | Kugler et al. | |
| 8,202,246 B2 | 6/2012 | Kugler et al. | |
| 8,323,261 B2 | 12/2012 | Kugler et al. | |
| 8,337,425 B2 | 12/2012 | Olson et al. | |
| 8,512,310 B2 | 8/2013 | Kugler et al. | |
| 9,402,981 B2 * | 8/2016 | Anderson | A61M 25/104 |
| 9,446,222 B2 * | 9/2016 | Silvestro | A61M 29/02 |
| 2001/0000041 A1 | 3/2001 | Selmon et al. | |
| 2001/0012924 A1 | 8/2001 | Milo et al. | |
| 2002/0103459 A1 | 8/2002 | Sparks et al. | |
| 2002/0128677 A1 | 9/2002 | Duerig et al. | |
| 2003/0109809 A1 | 6/2003 | Jen et al. | |
| 2003/0120195 A1 | 6/2003 | Milo et al. | |
| 2003/0139763 A1 | 7/2003 | Duerig et al. | |
| 2004/0167554 A1 | 8/2004 | Simpson et al. | |
| 2004/0230219 A1 | 11/2004 | Roucher, Jr. | |
| 2005/0075662 A1 * | 4/2005 | Pedersen | A61B 17/22 606/194 |
| 2005/0149062 A1 | 7/2005 | Carroll | |
| 2005/0171478 A1 | 8/2005 | Selmon et al. | |
| 2006/0015134 A1 * | 1/2006 | Trinidad | A61B 17/320725 606/194 |
| 2006/0094930 A1 | 5/2006 | Sparks et al. | |
| 2006/0167437 A1 | 7/2006 | Valencia | |
| 2006/0184011 A1 | 8/2006 | Macaulay et al. | |
| 2006/0276749 A1 | 12/2006 | Selmon et al. | |
| 2007/0093779 A1 | 4/2007 | Kugler et al. | |
| 2007/0093780 A1 | 4/2007 | Kugler et al. | |
| 2007/0093781 A1 | 4/2007 | Kugler et al. | |
| 2007/0093782 A1 | 4/2007 | Kugler et al. | |
| 2007/0208368 A1 | 9/2007 | Katoh et al. | |
| 2007/0265596 A1 | 11/2007 | Jen et al. | |
| 2008/0033423 A1 | 2/2008 | Peacock | |
| 2008/0125748 A1 | 5/2008 | Patel | |
| 2008/0154172 A1 | 6/2008 | Mauch | |
| 2008/0200896 A1 | 8/2008 | Shmulewitz et al. | |
| 2008/0228171 A1 | 9/2008 | Kugler et al. | |
| 2008/0243065 A1 | 10/2008 | Rottenberg et al. | |
| 2008/0243067 A1 | 10/2008 | Rottenberg et al. | |
| 2008/0249397 A1 | 10/2008 | Kapadia | |
| 2009/0005755 A1 | 1/2009 | Keith et al. | |
| 2009/0054837 A1 * | 2/2009 | Von Holst | A61L 29/16 604/103.08 |
| 2009/0088685 A1 * | 4/2009 | Kugler | A61B 17/221 604/101.01 |
| 2009/0093791 A1 | 4/2009 | Heuser | |
| 2009/0124899 A1 | 5/2009 | Jacobs et al. | |
| 2009/0209910 A1 * | 8/2009 | Kugler | A61B 17/11 604/103.1 |
| 2009/0230167 A1 | 9/2009 | Xiao et al. | |
| 2009/0254107 A1 | 10/2009 | Katoh et al. | |
| 2009/0264826 A1 | 10/2009 | Thompson | |
| 2009/0292296 A1 | 11/2009 | Pansky et al. | |
| 2009/0299171 A1 | 12/2009 | Duffy et al. | |
| 2009/0299402 A1 | 12/2009 | Orihashi et al. | |
| 2010/0063534 A1 * | 3/2010 | Kugler | A61B 17/221 606/200 |
| 2010/0069945 A1 * | 3/2010 | Olson | A61B 17/11 606/185 |
| 2010/0125244 A1 | 5/2010 | McAndrew | |
| 2010/0317973 A1 | 12/2010 | Nita | |
| 2011/0034904 A1 * | 2/2011 | Stivland | A61M 25/104 604/524 |
| 2011/0112564 A1 | 5/2011 | Wolf | |
| 2011/0144677 A1 | 6/2011 | Ward et al. | |
| 2011/0166591 A1 | 7/2011 | Katoh et al. | |
| 2013/0006282 A1 | 1/2013 | Wilkinson | |
| 2013/0072957 A1 * | 3/2013 | Anderson | A61M 25/104 606/194 |
| 2015/0250988 A1 * | 9/2015 | Dib | A61M 25/104 604/509 |
| 2015/0250991 A1 * | 9/2015 | Silvestro | A61M 29/02 606/194 |

\* cited by examiner

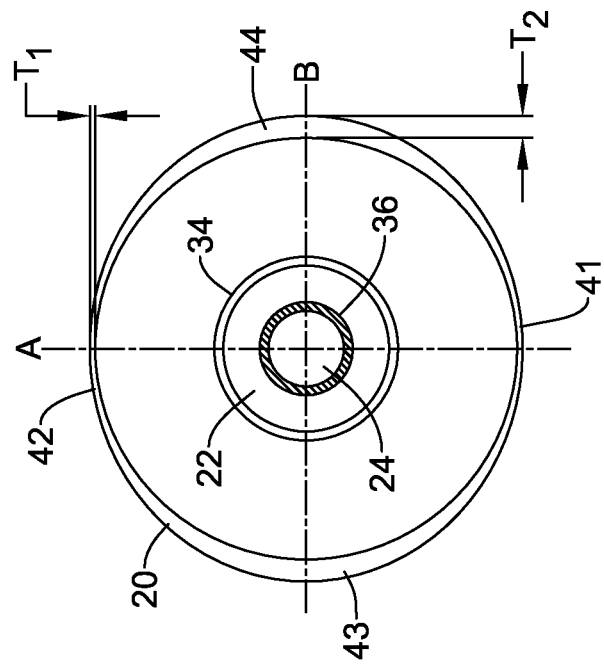
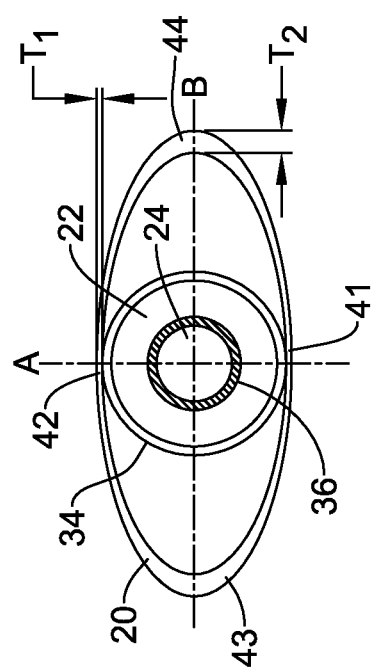
Figure 3A
Figure 3B

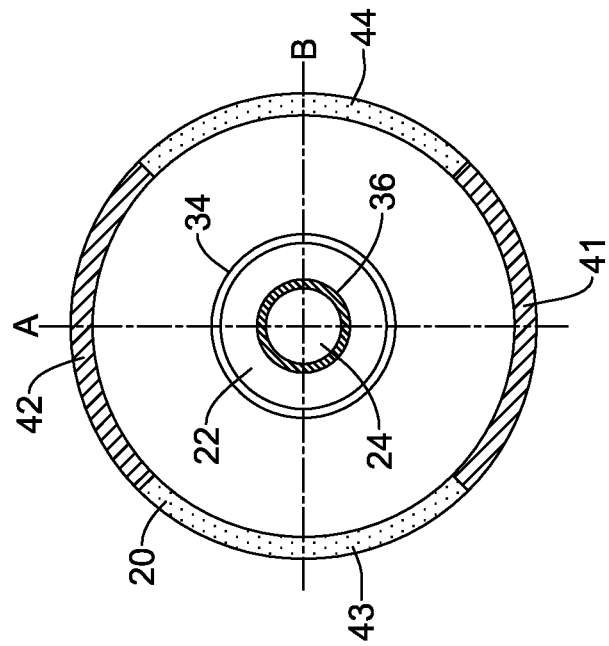
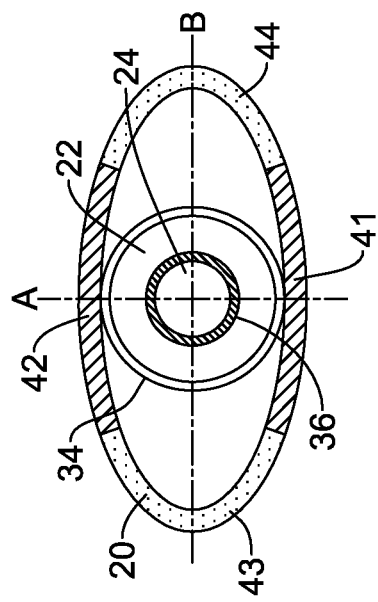
Figure 4B
Figure 4A

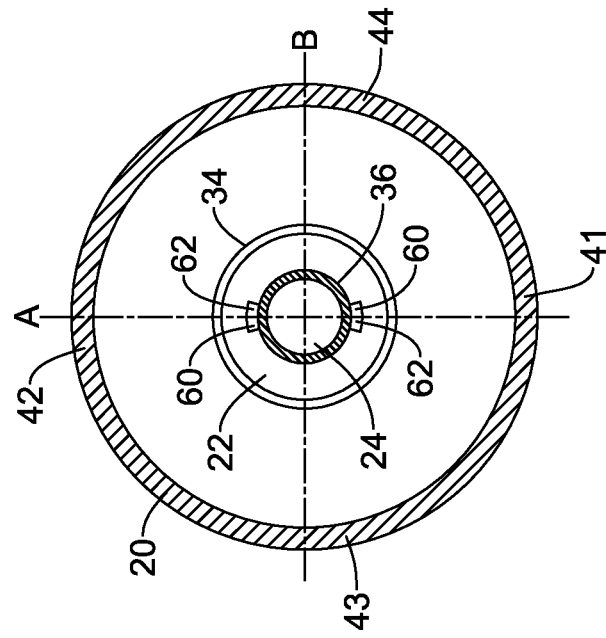
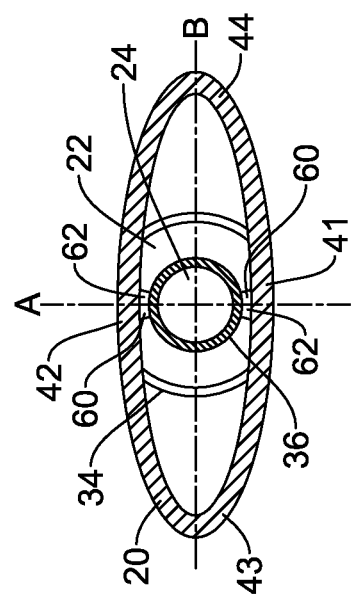
Figure 6B
Figure 6A

SUBINTIMAL RE-ENTRY CATHETER WITH SHAPE CONTROLLED BALLOON

CROSS REFERENCE TO RELATED APPLICATION

This application claims the benefit of U.S. Provisional Application Ser. No. 61/781,150, filed Mar. 14, 2013, the entire disclosure of which is incorporated herein by reference.

TECHNICAL FIELD

The disclosure is directed to devices and methods for recanalization of an occluded blood vessel. More particularly, the disclosure is directed to devices and methods for re-entry into the true lumen from the extraluminal or subintimal space of a blood vessel.

BACKGROUND

Chronic total occlusion (CTO) is an arterial vessel blockage that obstructs blood flow through the vessel, and can occur in both coronary and peripheral arteries. In some instances, it may be difficult or impossible to pass through the CTO with a medical device in an antegrade direction to recanalize the vessel. Accordingly, techniques have been developed for creating a subintimal pathway (i.e., a pathway between the intimal and adventitial tissue layers of the vessel) around the occlusion and then re-entering the true lumen of the vessel distal of the occlusion in an attempt to recanalize the vessel. In some instances re-entering the true lumen from the subintimal space and/or recanalization can be difficult. Accordingly, it is desirable to provide alternative recanalization devices and/or methods of recanalizing a blood vessel in which a CTO is present.

SUMMARY

The disclosure is directed to several alternative designs, materials and methods of manufacturing medical device structures and assemblies, and uses thereof.

Accordingly, one illustrative embodiment is a recanalization catheter for facilitating re-entry into a lumen of a blood vessel from a subintimal space. The catheter includes an inflatable balloon and an elongate shaft extending distally from a hub assembly along a longitudinal axis to the inflatable balloon. The elongate shaft includes a guidewire lumen having a distal opening and a lateral opening in a distal region of the elongate shaft proximal of the distal opening. The elongate shaft also includes an inflation lumen in fluid communication with the inflatable balloon. The inflatable balloon is configured to be inflated in the subintimal space to a first inflation state at inflation pressures below a threshold inflation pressure and inflated to a second inflation state at inflation pressures above the threshold inflation pressure. The inflatable balloon is configured to orient the lateral opening toward the lumen of the blood vessel when the inflatable balloon is inflated to the first inflation state.

Another illustrative embodiment is a recanalization catheter for facilitating re-entry into a lumen of a blood vessel from a subintimal space. The catheter includes an elongate shaft extending distally from a hub assembly and an inflatable balloon mounted on a distal region of the elongate shaft. The inflatable balloon is configured to be inflated in the subintimal space to a first inflation state at inflation pressures below a threshold inflation pressure and inflated to a second inflation state at inflation pressures above the threshold inflation pressure. The catheter also includes means for retaining the inflatable balloon in the first inflatable state until the inflatable balloon is inflated to an inflation pressure above the threshold inflation pressure.

Yet another illustrative embodiment is a method of recanalizing a blood vessel having an occlusion therein. The method includes advancing a distal region of a catheter shaft including an inflatable balloon mounted thereon into a subintimal space between a first tissue layer and a second tissue layer of a wall of a blood vessel. The inflatable balloon is then inflated to a first inflation state in the subintimal space by inflating the inflatable balloon to a first inflation pressure below a threshold inflation pressure to orient a lateral port in the distal region of the catheter shaft toward a lumen of the blood vessel distal of the occlusion. A penetration member is then advanced from the lateral port of the catheter shaft to penetrate through the first tissue layer into the lumen of the blood vessel. Thereafter, the inflatable balloon is inflated to a second inflation state different from the first inflation state by inflating the inflatable balloon to a second inflation pressure above the threshold inflation pressure.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIGS. 3A and 3B are exemplary cross-sectional views of another exemplary catheter apparatus having the balloon inflated to a first inflated state and a second inflated state, respectively;

FIGS. 4A and 4B are exemplary cross-sectional views of another exemplary catheter apparatus having the balloon inflated to a first inflated state and a second inflated state, respectively;

FIGS. 6A and 6B are exemplary cross-sectional views of another exemplary catheter apparatus having the balloon inflated to a first inflated state and a second inflated state, respectively;

Figure 1:
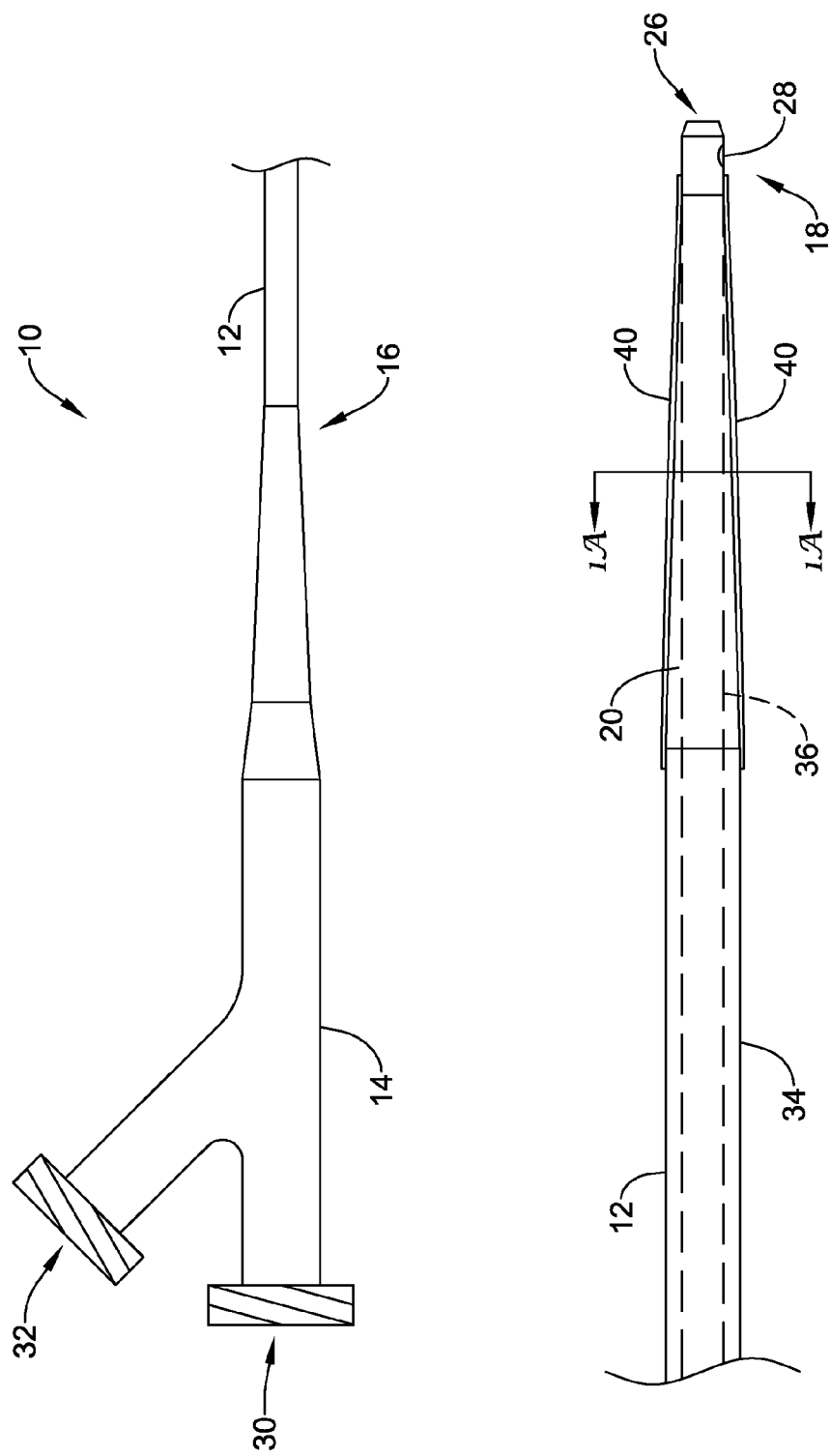
FIG. 1 is a plan view of an exemplary catheter apparatus for recanalization of a blood vessel having a balloon inflated to a first inflated state.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary recanalization catheter 10 is illustrated at FIG. 1. The recanalization catheter 10 may include a catheter shaft 12 extending from a hub assembly 14 at a proximal end 16 of the catheter shaft 12 to an inflatable balloon 20 mounted on a distal region of the catheter shaft 12 proximate the distal end 18 of the catheter shaft 12.

The catheter 10 may be configured to be advanced over a guidewire for delivery to a remote location in the vasculature of a patient. For example, in some instances the catheter 10 may be configured as an over-the-wire (OTW) catheter having a guidewire lumen 24 (see FIG. 1A) extending through the entire length of the catheter 10 from a distal opening or port 26 at a distal tip of the catheter 10 to a proximal guidewire port 30 in the hub assembly 14. In other instances, the catheter 10 may be configured as a single-operator-exchange (SOE) catheter having a guidewire lumen 24 extending from a distal port 26 to a proximal guidewire port (not shown) located a short distance proximal of the expandable winged structure 20 and distal of the hub assembly 14. In such a configuration, the guidewire may extend through the guidewire lumen 24 between the distal opening or port 26 and the proximal port, and extend along an exterior of the catheter shaft 12 proximal of the proximal port to the proximal end 16 of the catheter shaft 12. It is noted that in instances in which the catheter 10 is an SOE catheter, the hub assembly 14 may not include a proximal guidewire port 30.

The catheter shaft 12 may also include an inflation lumen 22 (see FIG. 1A) in fluid communication with the inflatable balloon 20 configured to deliver an inflation fluid to the inflatable balloon 20 to inflate the inflatable balloon 20 and/or withdraw an inflation fluid from the inflatable balloon to deflate the inflatable balloon 20 during use. The inflation lumen 22 may extend from an inflation port 32 in the hub assembly 14, through the catheter shaft 12 to the interior of the inflatable balloon 20.

The catheter 10 may also include a lateral opening or port 28 opening out on a lateral side of the catheter shaft 12 in the distal region. The lateral port 28, which may be located proximal of the distal opening or port 26, may be positioned at any desired location in the distal region of the catheter shaft 12. For example, as shown in FIG. 1, the lateral port 28 may be located distal of the balloon 20 in some instances. In other embodiments, the lateral port 28 may be located proximal of the balloon 20, or at a location along the length of the balloon 20 itself. The lateral port 28 may be configured to permit a re-entry device or penetration member, such as a guidewire, stylet, cannula, etc., to be advanced out of the lateral port 28 during a recanalization procedure to penetrate through one or more tissue layers of a vessel wall to re-enter into the true lumen of a blood vessel from a subintimal space formed between tissue layers in the vessel wall. Thus, the lateral port 28 may permit a re-entry device to be advanced out the lateral port 28 in a direction laterally away from the longitudinal axis of the catheter shaft 12 and guidewire lumen 24. In some instances, the lateral port 28 may be in communication with the guidewire lumen 24 such that a re-entry device may be advanced through the guidewire lumen 24 and then be directed outward through the lateral port 28. However, in other instances, the catheter shaft 12 may include a separate lumen, e.g., a re-entry device lumen, in communication with the lateral port 28 for advancement of a re-entry device therethrough and out the lateral port 28.

Figure 1A:
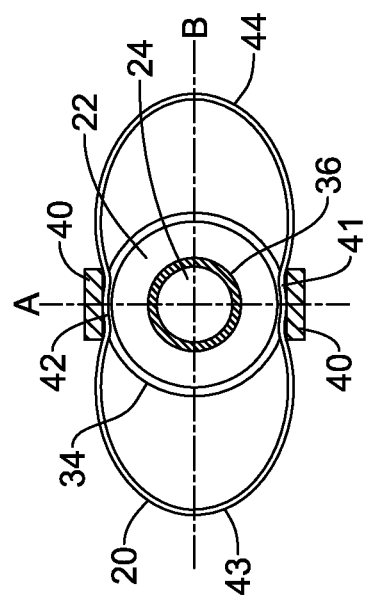
FIG. 1A is a cross-sectional view of the catheter apparatus of FIG. 1 taken along line 1A-1A.

The catheter shaft 12 may be formed of any desired construction, having the guidewire lumen 24, the inflation lumen 22, and/or one or more additional lumens extending therethrough, if desired. For example, as shown in FIG. 1A, the catheter shaft 12 may include an outer tubular member 34 and an inner tubular member 36 extending through the lumen of the outer tubular member 34. In such a construction, the lumen of the inner tubular member 36, e.g., the guidewire tube, may define the guidewire lumen 24, and the space between the inner surface of the outer tubular member 34 and the outer surface of the inner tubular member 36 may define the inflation lumen 22. In some instances, the inner tubular member 36 may extend coaxially with the outer tubular member 34, with the annular space formed therebetween defining the inflation lumen 22. The inner tubular member 36 may extend distal of the distal end of the outer tubular member 34, with the proximal waist of the inflatable balloon 20 secured to the distal end of the outer tubular member 34 and the distal waist of the inflatable balloon 20 secured to the distal end of the inner tubular member 36 proximate the distal tip of the catheter shaft 12. Accordingly, the inner tubular member 36, e.g., the guidewire tube, may extend through the interior of the inflatable balloon 20. In other instances, the catheter shaft 12, or portions thereof, may be an extruded shaft having the guidewire lumen 24, the inflation lumen 22, and/or one or more additional lumens formed therein. In such instances, the guidewire tube defining the guidewire lumen 24 may extend through the interior of the inflatable balloon 20.

Figure 2A:
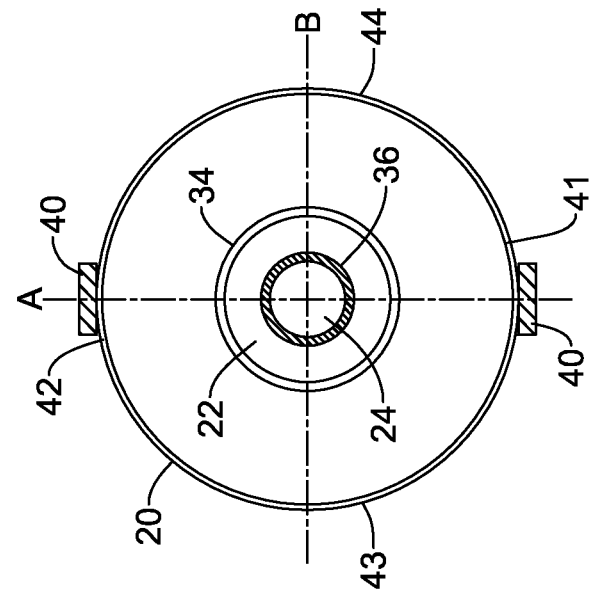
FIG. 2A is a cross-sectional view of the catheter apparatus of FIG. 2 taken along line 2A-2A.
Figure 2:
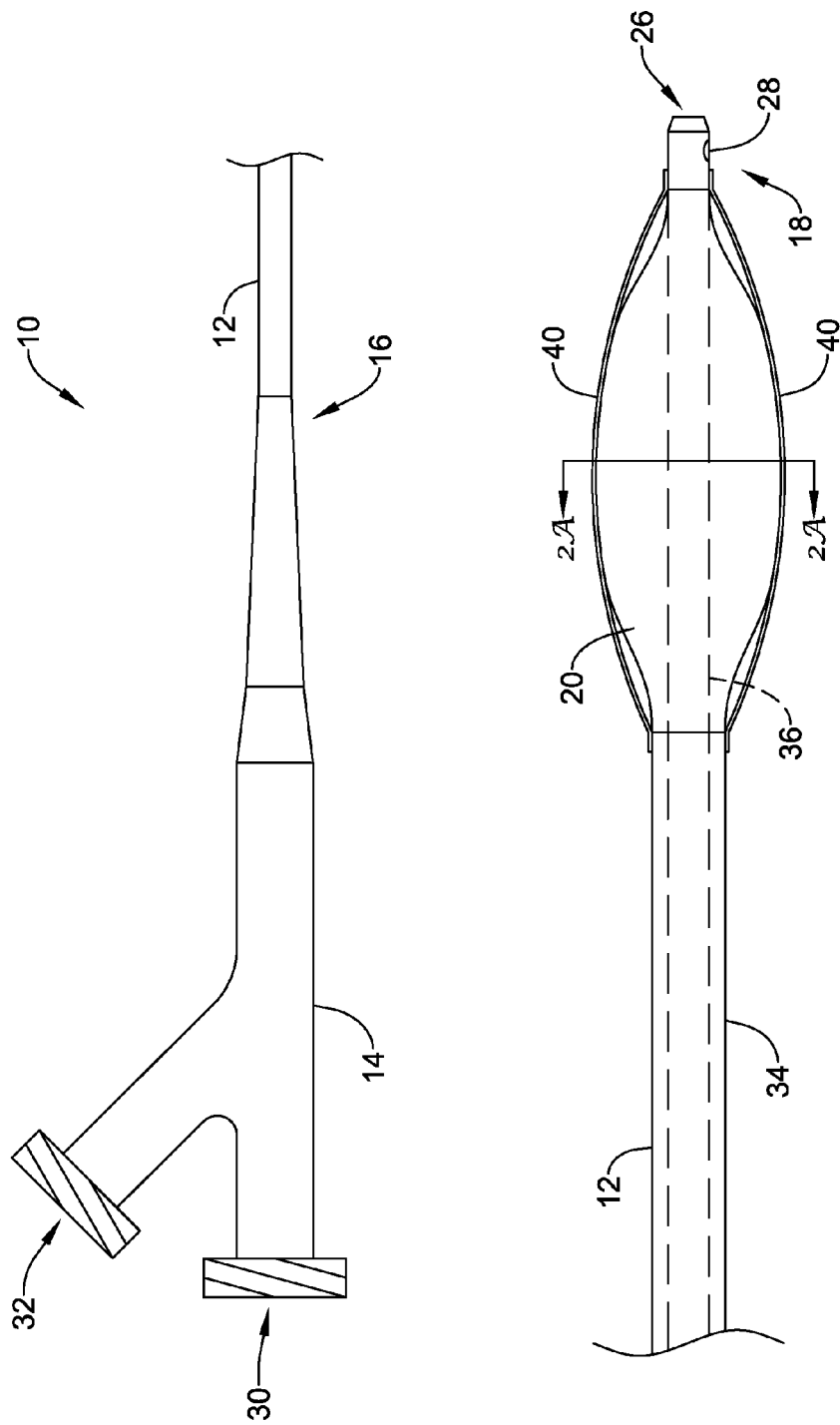
FIG. 2 is a plan view of the exemplary catheter apparatus of FIG. 1 having the balloon inflated to a second inflated state.

The catheter 10 may be configured such that the inflatable balloon 20 may be controllably inflated to a first inflated state or stage, shown in FIG. 1, or a second inflated stage or stage, shown in FIG. 2. For example, the inflatable balloon 20 may be configured to be inflated in the subintimal space formed in a vessel wall to the first inflation state at inflation pressures below a threshold inflation pressure and inflated to the second inflation state at inflation pressures above the threshold inflation pressure. Accordingly, the configuration of the inflatable balloon 20 at the first inflation state or stage may orient the lateral port 28 toward the lumen of the blood vessel when the inflatable balloon 20 is inflated to the first inflation state.

The shape of the inflatable balloon 20 in the first inflation state or stage may be different than the shape of the inflatable balloon in the second inflation state or stage. For example, as shown in FIGS. 1A and 2A, in the first inflation state the inflatable balloon 20 may have a flattened cross-sectional profile, and in the second inflation state the inflatable balloon may have a circular cross-sectional profile, respectively. The shape of the inflatable balloon in the first inflation state, shown in FIG. 1A, may facilitate orienting the lateral port 28 toward the lumen of the blood vessel when the inflatable balloon 20 is inflated to the first inflation state. For example, in the first inflation state, the inflatable balloon may include a first segment 41 configured to be oriented radially toward the lumen of the blood vessel from the longitudinal axis with the lateral port 28, a second segment 42 configured to be oriented radially away from the lumen of the blood vessel from the longitudinal axis, and third and fourth segments 43, 44 interposed between the first and second segments 41, 42. In other words, as shown in FIG. 1A, a plane A extending parallel to and along the longitudinal axis of the guidewire lumen 24 and passing through the lateral port 28 may pass through, e.g., bisect, the first and second segments 41, 42, and a plane B extending parallel to and along the longitudinal axis and perpendicular to the plane A may pass through, e.g., bisect, the third and fourth segments 43, 44. In such a configuration, the third and fourth segments 43, 44 may be located further from the longitudinal axis of the catheter shaft 12 and/or the guidewire lumen 24 (e.g., the intersection of plane A and plane B) than the first and second segments 41, 42 in the first inflation state. With such a configuration, inflation of the balloon 20 between tissue layers of the vessel wall may automatically orient the balloon 20 with either the first or second segment 41, 42 facing or oriented toward the lumen of the vessel. In the second inflation state, shown in FIG. 2A, the first, second, third and fourth segments 41, 42, 43, 44 may be located about equidistantly from the longitudinal axis of the catheter shaft 12 and/or the guidewire lumen 24 (e.g., the intersection of plane A and plane B).

In some embodiments, the threshold inflation pressure may be in the range of about 4 ATM to about 6 ATM, in the range of about 4 ATM to about 5 ATM, in the range of about 5 ATM to about 6 ATM, about 4 ATM, about 5 ATM, or about 6 ATM, for example. Accordingly, the inflatable balloon 20 may be configured to be in the first inflation state at inflation pressures of 4 ATM or below, for example between about 2 ATM to about 4 ATM, while the inflatable balloon 20 may be configured to be in the second inflation state at inflation pressures of 6 ATM or greater. Thus, during use, the inflatable balloon 20 may initially be inflated to a first inflation pressure of 4 ATM or below, for example inflated to an inflation pressure of between about 2 ATM to about 4 ATM, to inflate the inflatable balloon 20 to the first inflation state. When desired, the inflatable balloon may be inflated above the threshold inflation pressure, such as inflated to a second inflation pressure of greater than 6 ATM, to inflate the inflatable balloon 20 to the second inflation state. Thus, the shape of the balloon 20, which may be controlled based on the inflation pressure within the balloon 20, may be converted from the shape of the balloon 20 in the first inflation state to the shape of the balloon 20 in the second inflation state.

It may be further evidenced from comparing FIGS. 1A and 2A, that the third and fourth segments 43, 44 may be configured to have a first radius of curvature in the first inflatable state and a second radius of curvature greater than the first radius of curvature in the second inflatable state when the inflatable balloon 20 is inflated to an inflation pressure above the threshold inflation pressure. Furthermore, the first and second segments 41, 42 may be configured to have a first radius of curvature in the first inflatable state and a second radius of curvature less than the first radius of curvature in the second inflatable state when the inflatable balloon 20 is inflated to an inflation pressure above the threshold inflation pressure.

The catheter 10 may include means for retaining the inflatable balloon 20 in the first inflation state until the inflatable balloon 20 is inflated to an inflation pressure above the threshold inflation pressure. For example, in some embodiments, the catheter 10 may include a structural feature configured to resist expansion of the first and second balloon segments 41, 42 radially away from the longitudinal axis (e.g., the intersection of plane A and plane B), and thus the inner tubular member 36 until the pressure within the balloon 20 exceeds the threshold inflation pressure. In other embodiments, the structure of the balloon 20 may be configured to resist expansion of the first and second balloon segments 41, 42 radially away from the longitudinal axis (e.g., the intersection of plane A and plane B), and thus the inner tubular member 36, until the pressure within the balloon 20 exceeds the threshold inflation pressure. In some instances, a structural component may be located exterior of the inflatable balloon 20, interior of the inflatable balloon 20, or imbedded within the inflatable balloon 20 to resist expansion of the first and second balloon segments 41, 42 until the inflatable balloon 20 is inflated above the threshold inflation pressure. In some instances, in the first inflation state the inflatable balloon 20 may be secured to the catheter shaft 12 (e.g., the outer tubular member 34 and/or the inner tubular member 36) at the proximal and distal waists of the inflatable balloon 20, as well as one more intermediate locations along the body of the balloon 20 between the proximal and distal balloon waists, whereas, in the second inflation state the inflatable balloon 20 may only be secured to the catheter shaft 12 (e.g., the outer tubular member 34 and/or the inner tubular member 36) at the proximal and distal waists of the inflatable balloon 20. For example, the proximal waist of the balloon 20 may be secured to the outer tubular member 34 and the distal waist of the balloon 20 may be secured to the inner tubular member 34, while no intermediate portions of the balloon 20 along the body of the balloon 20 are secured to either the outer tubular member 34 or the inner tubular member 36.

Some suitable structures for resisting expansion of the first and second balloon segments 41, 42 radially away from the longitudinal axis (e.g., the intersection of plane A and plane B), and thus the inner tubular member 36, until the pressure within the balloon 20 exceeds the threshold inflation pressure, are illustrated in FIGS. 1A-2A, 3A-3B, 4A-4B, 5A-5B, 6A-6B, and 7A-7B. The cross-sections illustrated in these figures are taken through a central portion of the balloon 20, and thus illustrate a cross-section of the inner tubular member 36 extending through the balloon 20, as well as viewing the distal end of the outer tubular member 34 which ends proximal of the location the cross-section is taken through the balloon 20 (e.g., proximate the proximal waist of the balloon 20).

The catheter 10 shown in FIGS. 1 and 2 includes stiffening members 40 extending longitudinally along the inflatable balloon 20 on opposite sides of the balloon 20. The longitudinal stiffening members 40 are shown extending along an exterior surface of the inflatable balloon 20, however, in other instances, the longitudinal stiffening members 40 may extend along and be secured to an interior surface of the balloon 20 or the longitudinal stiffening members 40 may extend within the wall of the balloon 20, for example. The stiffening members 40 are shown extending the entire length of the balloon 20 with a proximal end attached to the outer tubular member 34 of the catheter shaft 12 proximate the proximal waist of the balloon 20 and a distal end attached to the inner tubular member 36 of the catheter shaft 12 proximate the distal waist of the balloon 20. However, in other instances the stiffening members 40 may extend distally from the outer tubular member 34 proximate the proximal waist of the balloon 20, with a distal end remaining unattached to the catheter shaft 12 or the stiffening members 40 may extend proximally from the inner tubular member 36 proximate the distal waist of the balloon 20, with a proximal end remaining unattached to the catheter shaft 12, if desired.

The stiffening members 40 may extend longitudinally along the first and second segments 41, 42 of the balloon 20 to resist radial expansion of the first and second segments 41, 42 at pressures below the threshold pressure. For example, the stiffening members 40 may have a sufficient stiffness to resist elastic deformation at inflation pressures below the threshold pressure. However, the stiffening members 40 may be configured to yield (e.g., elastically stretch/deform or plastically stretch/deform/break) at inflation pressures above the threshold pressure in order to permit the first and second segments 41, 42 to radially expand away from the longitudinal axis when the balloon 20 is inflated to a pressure above the threshold pressure. Thus, the stiffening members 40 may resist expansion of the balloon 20 along plane A while permitting expansion of the balloon 20 along plane B at inflation pressures below the threshold inflation pressure, as shown in FIG. 1A, but when the stiffening members 40 yield at inflation pressures above the threshold inflation pressure, the pressure within the balloon 20 may overcome the stiffness of the stiffening members 40 to expand the balloon 20 along plane A, as shown in FIG. 2A.

In other embodiments the balloon may be formed to have a first shape at the first inflation state and a different, second shape at the second inflation state. For example, the inflatable balloon 20 may be molded into a flat configuration (that will be maintained at inflation pressures below the threshold pressure) that will naturally convert to a circular shape when inflated above the threshold pressure. In other embodiments, the inflatable balloon 20 may initially be blow molded into a circular shape that the balloon 20 will assume at pressures above the threshold pressure. In a secondary formation process, the balloon 20 may be re-molded or heat shrunk to set a flat shape in the balloon 20 that the balloon 20 will maintain at pressures below the threshold pressure.

FIGS. 3A-3B illustrate an alternative embodiment in which the balloon 20 may be configured to resist radial expansion of the first and second segments 41, 42 at pressures below the threshold pressure. For example, the first and second segments 41, 42 may be formed (such as in an extrusion and/or molding process) to have a first thickness T1 and the third and fourth segments 43, 44 may be formed (such as in an extrusion and/or molding process) to have a second thickness T2 different than the first thickness T1. In the illustrated embodiment, the first and second segments 41, 42 have a thickness T1 less than the thickness T2 of the third and fourth segments 43, 44, however, in other instances the first and second segments 41, 42 may have a thickness T1 greater than the thickness T2 of the third and fourth segments 43, 44.

In such an embodiment, the first and second segments 41, 42 may be configured to elastically deform while the third and fourth segments 43, 44 do not deform or deform to a lesser extent at inflation pressures below the threshold pressure, thus resisting expansion of the balloon 20 along plane A while permitting expansion of the balloon 20 along plane B at inflation pressures below the threshold inflation pressure, as shown in FIG. 3A. Thereafter, the third and fourth segments 43, 44 may elastically deform upon inflating the balloon 20 to a pressure above the threshold pressure, which may permit the first and second segments 41, 42 to radially expand away from the longitudinal axis to the second inflated state or stage shown in FIG. 3B.

As shown in FIGS. 3A-3B, the third and fourth curved segments 43, 44 may be configured to have a first radius of curvature in the first inflatable state (shown in FIG. 3A) and a second radius of curvature greater than the first radius of curvature in the second inflatable state (shown in FIG. 3B) when the inflatable balloon 20 is inflated to an inflation pressure above the threshold inflation pressure. Correspondingly, the first and second curved segments 41, 42 may be configured to have a first radius of curvature in the first inflatable state (shown in FIG. 3A) and a second radius of curvature less than the first radius of curvature in the second inflatable state (shown in FIG. 3B) when the inflatable balloon 20 is inflated to an inflation pressure above the threshold inflation pressure.

FIGS. 4A-4B illustrate another alternative embodiment in which the balloon 20 may be configured to resist radial expansion of the first and second segments 41, 42 at pressures below the threshold pressure. For example, the first and second segments 41, 42 may be formed (such as in an extrusion and/or molding process) to have a first stiffness or hardness and the third and fourth segments 43, 44 may be formed (such as in an extrusion and/or molding process) to have a second stiffness or hardness different than the first stiffness or hardness. In the illustrated embodiment, the first and second segments 41, 42 may be considered hard segments and the third and fourth segments 43, 44 may be considered soft segments, with the first and second segments 41,42 having a stiffness or hardness greater than the stiffness or hardness of the third and fourth segments 43, 44, however, in other instances the first and second segments 41, 42 may have a hardness than the hardness of the third and fourth segments 43, 44. In such an instance, the first and second segments 41, 42 may be considered soft segments and the third and fourth segments 43, 44 may be considered hard segments. In describing the segments as hard and soft, it is intended to relate the stiffness or hardness of the various segments in relative terms. In such an embodiment, the first and second segments 41, 42 may be formed of a first polymer material and the third and fourth segments 43, 44 may be formed of a second polymer material, different from the first polymer material to achieve the difference in hardness or stiffness between the segments. In some instances, the stiffer segments may include a filler or additive to enhance the hardness or stiffness.

In such an embodiment, the third and fourth segments 43, 44 may be configured to elastically deform or flex while the first and second segments 41, 42 do not deform or deform to a lesser extent at inflation pressures below the threshold pressure, thus resisting expansion of the balloon 20 along plane A while permitting expansion of the balloon 20 along plane B at inflation pressures below the threshold inflation pressure, as shown in FIG. 4A. Thereafter, the first and second segments 41, 42 may elastically deform (e.g., flex or bend) upon inflating the balloon 20 to a pressure above the threshold pressure, which may permit the first and second segments 41, 42 to radially expand away from the longitudinal axis to the second inflated state or stage shown in FIG. 4B.

As shown in FIGS. 4A-4B, the first and second curved segments 41, 42 may be configured to have a first radius of curvature in the first inflatable state (shown in FIG. 4A) and a second radius of curvature less than the first radius of curvature in the second inflatable state (shown in FIG. 4B) when the inflatable balloon 20 is inflated to an inflation pressure above the threshold inflation pressure. Correspondingly, the third and fourth curved segments 43, 44 may be configured to have a first radius of curvature in the first inflatable state (shown in FIG. 4A) and a second radius of curvature greater than the first radius of curvature in the second inflatable state (shown in FIG. 4B) when the inflatable balloon 20 is inflated to an inflation pressure above the threshold inflation pressure.

Figure 5B:
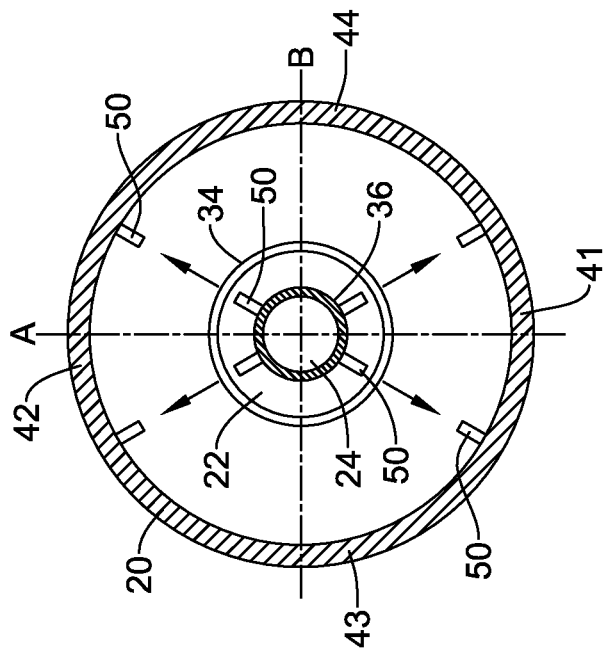
FIGS. 5A and 5B are exemplary cross-sectional views of another exemplary catheter apparatus having the balloon inflated to a first inflated state and a second inflated state, respectively.
Figure 5A:
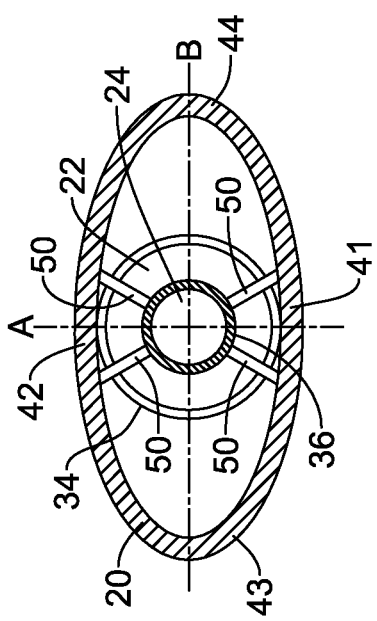

FIGS. 5A-5B illustrate an embodiment including a structural feature interior of the inflatable balloon 20 configured to resist radial expansion of the first and second segments 41, 42 at pressures below the threshold pressure. For example, one or more, or a plurality of interior struts 50 may extend between the wall of the balloon 20 and the inner tubular member 36 (e.g., the guidewire tube) extending through the balloon 20. In some instances, the struts 50 may be formed as a unitary portion of the balloon 20, or the struts 50 may be separate members attached between the balloon 20 and the inner tubular member 36 subsequent to formation of the balloon 20 in other instances.

In such an embodiment, the struts 50, which may extend radially from the inner tubular member 36 to the first and second segments 41, 42 of the balloon 20, may resist radial expansion of the first and second segments 41, 42 at pressures below the threshold pressure. For example, the struts 50 may have a sufficient strength to resist yielding (e.g., elastic or plastic deformation or breaking) at inflation pressures below the threshold pressure. However, the struts 50 may be configured to yield (e.g., elastically stretch/deform or plastically stretch/deform/break) at inflation pressures above the threshold pressure in order to permit the first and second segments 41, 42 to radially expand away from the longitudinal axis when the balloon 20 is inflated to a pressure above the threshold pressure. Thus, the struts 50 may resist expansion of the balloon 20 along plane A while permitting expansion of the balloon 20 along plane B at inflation pressures below the threshold inflation pressure, as shown in FIG. 5A, but when the struts 50 yield at inflation pressures above the threshold inflation pressure, the pressure within the balloon 20 may overcome the strength of the struts 50 to expand the balloon 20 along plane A, as shown in FIG. 5B. In some instances, the struts 50 or portions thereof, which may be attached between the balloon 20 and the inner tubular member 36 in the first inflation state, may detach from the balloon 20 and/or the inner tubular member 36 as the pressure is increased above the threshold pressure. For example, as shown in FIG. 5B, in some instances, the struts 50 may be configured to be broken from the inner tubular member 36 and/or the balloon 20 when the inflatable balloon 20 is inflated to an inflation pressure above the threshold inflation pressure.

FIGS. 6A-6B and 7A-7B illustrate embodiments wherein the first and second segments 41, 42 of the inflatable balloon 20 are bonded to the inner tubular member 36 (e.g., the guidewire tube) at bonding locations 60, 70 at pressures below the threshold pressure to resist radial expansion of the first and second segments 41, 42.

Figure 7B:
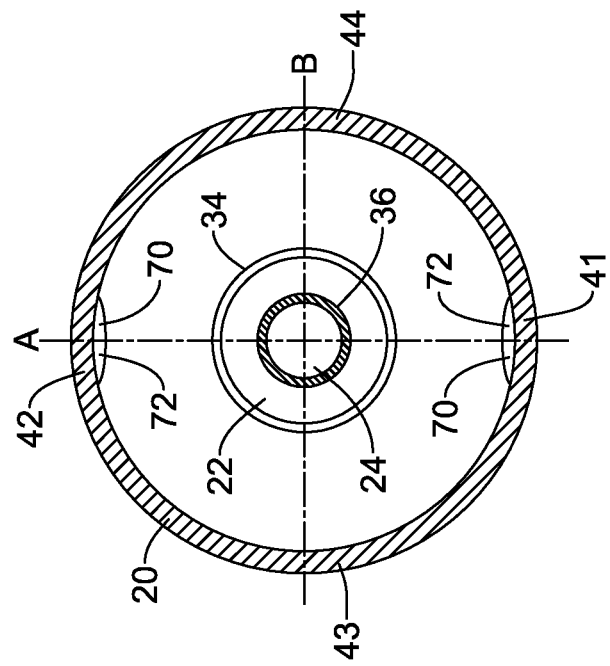
FIGS. 7A and 7B are exemplary cross-sectional views of another exemplary catheter apparatus having the balloon inflated to a first inflated state and a second inflated state, respectively
Figure 7A:
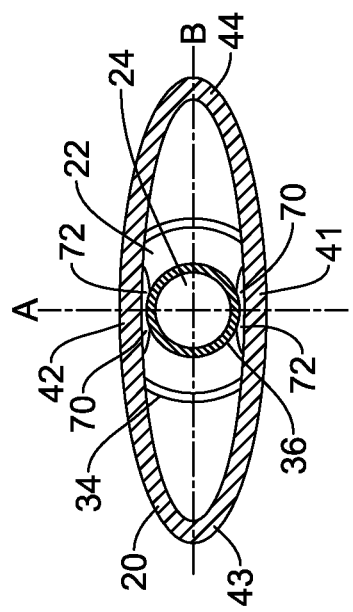

In such embodiments, bonding locations 60, 70 may resist radial expansion of the first and second segments 41, 42 at pressures below the threshold pressure. For example, the bonding locations 60, 70 may have a sufficient strength to resist yielding at inflation pressures below the threshold pressure. However, the bonding locations 60, 70 may be configured to yield at inflation pressures above the threshold pressure in order to detach the first and second segments 41, 42 from the inner tubular member 36 and permit the first and second segments 41, 42 to radially expand away from the longitudinal axis when the balloon 20 is inflated to a pressure above the threshold pressure. Thus, the bonding locations 60, 70 may resist expansion of the balloon 20 along plane A while permitting expansion of the balloon 20 along plane B at inflation pressures below the threshold inflation pressure, as shown in FIGS. 6A and 7A, but when the bonding locations 60, 70 yield at inflation pressures above the threshold inflation pressure, the pressure within the balloon 20 may overcome the strength of the bonding locations 60, 70 to expand the balloon 20 along plane A, as shown in FIGS. 6B and 7B. Thus, the bonding locations 60, 70, which may be attached between the balloon 20 and the inner tubular member 36 in the first inflation state, may detach from the balloon 20 and/or the inner tubular member 36 as the pressure is increased above the threshold pressure.

In the embodiment of FIGS. 6A-6B, the bonding locations 60 may be provided as bonding layers 62 on the exterior of the inner tubular member 36 and then the first and second segments 41, 42 may be bonded thereto by bringing the first and second segments 41, 42 into contact with the bonding layers 62 at the bonding locations 60. For example, the inner tubular member 36 may be provided with an exterior layer 62 that may be bonded to the inner surface of the balloon 20. In some instances, the exterior layer 62 may be circumferentially disposed entirely around the inner tubular member 36 or the exterior layer 62 may be disposed at discrete locations about the circumference of the inner tubular member 36. For example, as shown in FIGS. 6A-6B, discrete bonding layers 62, extending longitudinally along the inner tubular member 36, may be located on opposite sides of the inner tubular member 36 in corresponding orientation with the first and second segments 41, 42 of the balloon 20. In some instances, the exterior bonding layer 62 may be extruded with the inner tubular member 36, or applied to the inner tubular member 36 in a subsequent process.

In the embodiment of FIGS. 7A-7B, the bonding locations 70 may be provided as bonding layers 72 on the interior of the first and second segments 41, 42 of the inflatable balloon 20 and then the inner tubular member 36 may be bonded thereto by bringing the bonding layers 72 at the bonding locations 70 into contact with the inner tubular member 36. For example, the inflatable balloon 20 may be provided with an interior layer 72 that may be bonded to the outer surface of the inner tubular member 36. In some instances, the interior layer 72 may be circumferentially disposed entirely around the balloon 20 or the interior layer 72 may be disposed at discrete locations about the circumference of the balloon 20. For example, as shown in FIGS. 7A-7B, discrete bonding layers 72, extending longitudinally along the balloon 20, may be located on opposite sides of the balloon 20, corresponding to the first and second segments 41, 42 of the balloon 20. In some instances, the interior bonding layer 72 may be extruded with the balloon 20, or applied to the balloon 20 in a subsequent process.

The bonding layers 62, 72 may be formed of any material permitting the first and second segments 41, 42 of the balloon 20 to be selectively bonded to the inner tubular member 36. For example, the bonding layer 62, 72 may a polymer having a lower melting temperature than the polymers of the inner tubular member 36 and the balloon, providing a low temperature tack feature. One suitable polymer material is Grilamid EA20HV1. The bonding layer 62, 72 may be heated above its melting temperature to bond to the balloon 20, and then cooled to provide the bond between the balloon 20 and the inner tubular member 36. The bond strength of the bonding material may be selected to fail when the pressure is increased above the threshold pressure, permitting the first and second segments 41, 42 to move radially outward away from the inner tubular member 36. In other instances, the bonding layer 62, 72 may be a pressure sensitive adhesive, such as an acrylic pressure sensitive adhesive, a polyurethane pressure sensitive adhesive, or other adhesive material, having a bonding strength selected to fail when the pressure is increased above the threshold pressure.

In such embodiments, the proximal waist and/or distal waist of the balloon 20 may be bonded to the catheter shaft 12 (e.g., the outer tubular member 34 and/or the inner tubular member 36) during a manufacturing process, and thereafter the first and second segments 41, 42 may be bonded to the catheter shaft 12 (e.g., the inner tubular member 36) at the desired bonding locations 60, 70 with the lateral port 28 appropriately oriented.

FIGS. 8-12 illustrate aspects of an exemplary method for recanalizing an occluded blood vessel using the catheter apparatus of FIG. 1. Although the catheter 10, including the stiffening members 40 is illustrated, it is understood that in other instances the catheter 10 may include another construction, such as those constructions illustrated herein, configured to retain the inflatable balloon 20 in the first inflation state until the inflatable balloon 20 is inflated to an inflation pressure above the threshold inflation pressure. For example, the catheter 10 may include a structural feature configured to resist radial expansion of the first and second balloon segments 41, 42 and/or the structure of the balloon 20 may be configured to resist radial expansion of the first and second balloon segments 41, 42 at pressures below the threshold inflation pressure.

As shown in FIGS. 8-12, a blood vessel 80 typically has three tissue layers, an innermost layer or intima layer (i.e., tunica intima) 82, an intermediate layer or media layer (i.e., tunica media) 84, and an outermost layer or adventitia layer (tunica adventitia) 86, with the media layer 84 positioned between the intima layer 82 and the adventitia layer 86. The intima layer 82 is a layer of endothelial cells lining the lumen 88 of the vessel 80, as well as a subendothelial layer made up of mostly loose connective tissue. The media layer 84 is a muscular layer formed primarily of circumferentially arranged smooth muscle cells. The adventitia layer 86, which forms the exterior layer of the vessel wall 80 is formed primarily of loose connective tissue made up of fibroblasts and associated collagen fibers.

Figure 8:
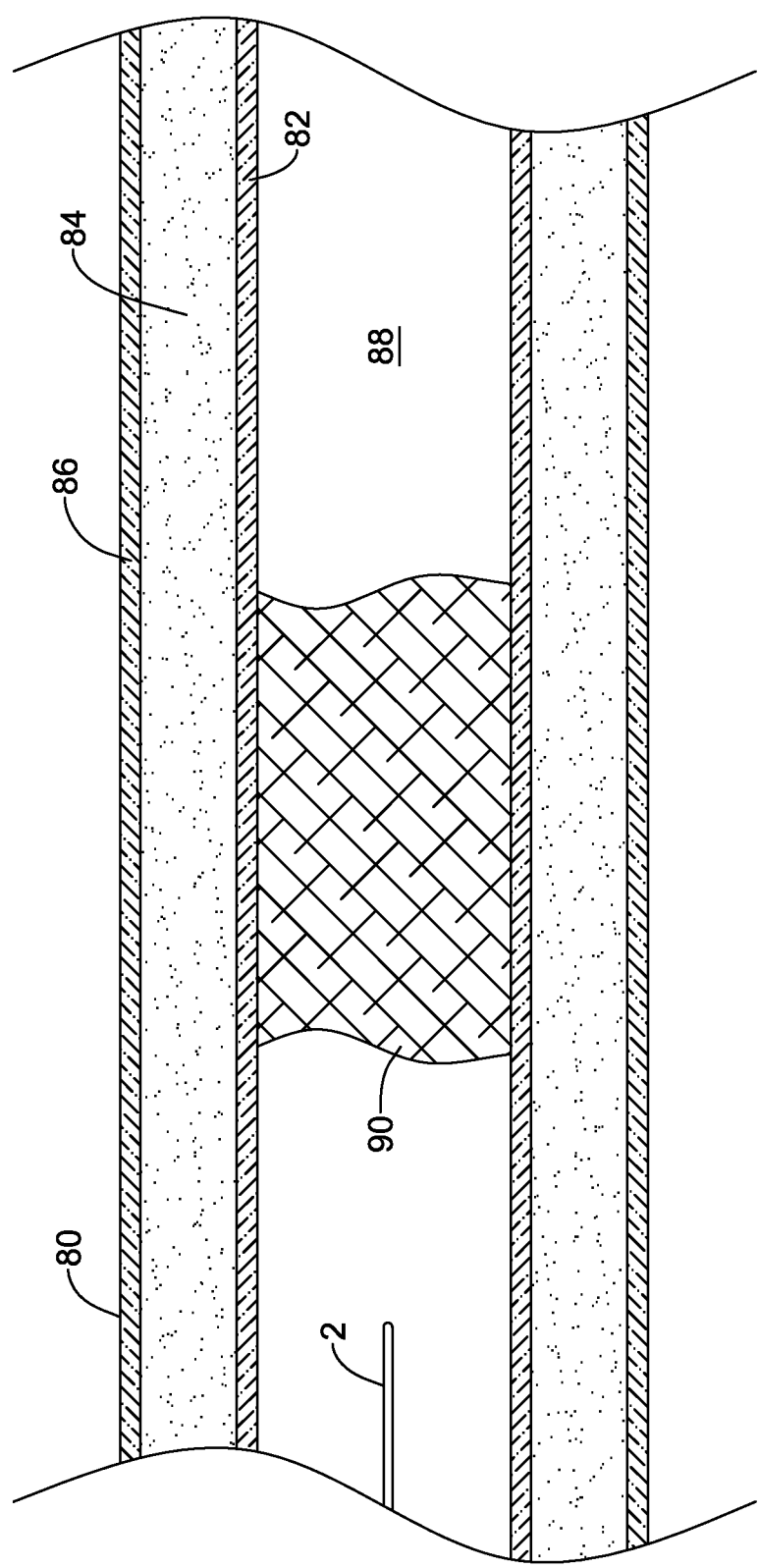
FIGS. 8-12 illustrate aspects of an exemplary method for recanalizing an occluded blood vessel using the catheter apparatus of FIG. 1.
Figure 9:
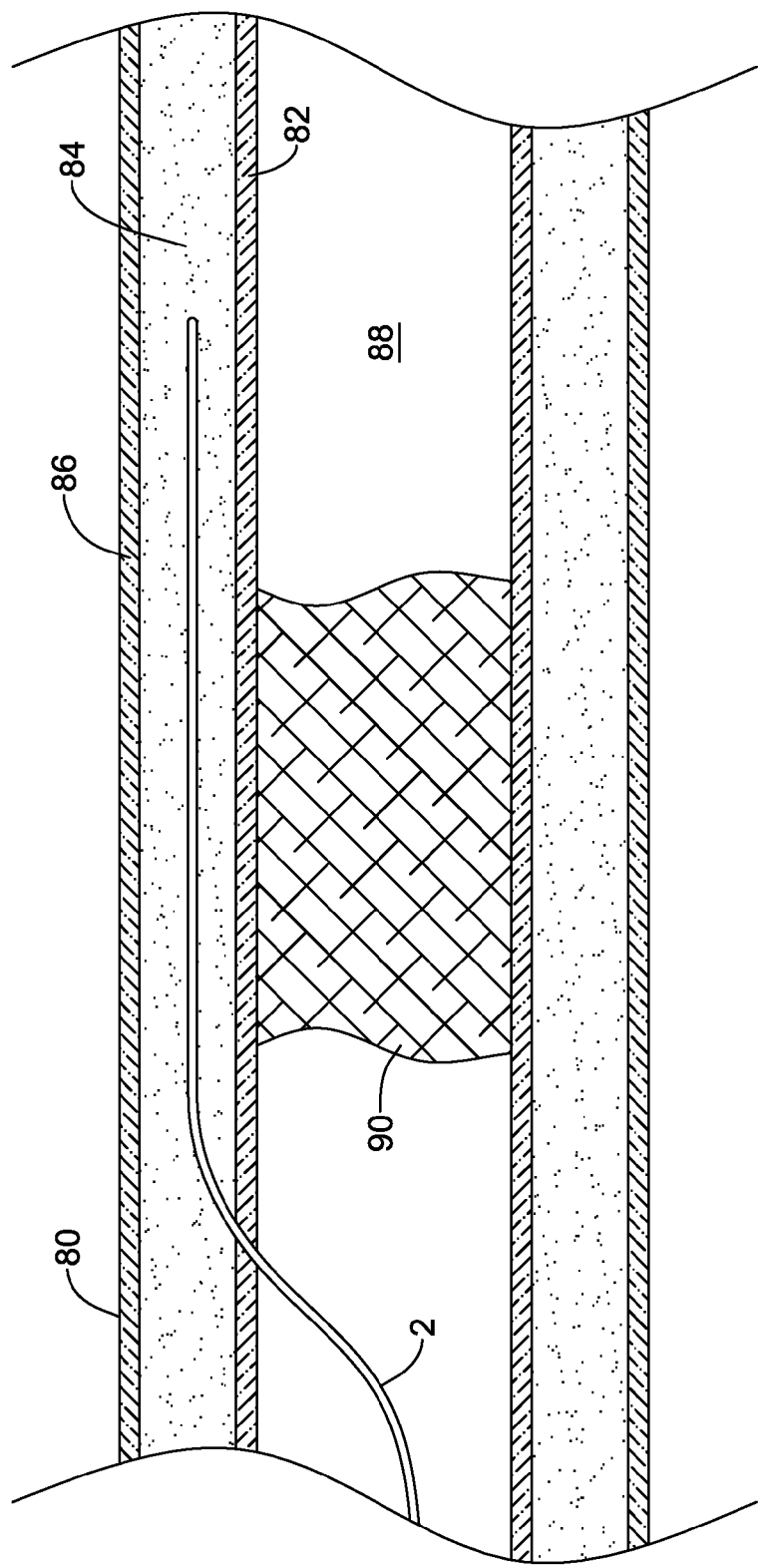

In some instances, it may be undesired, difficult or impossible to pass through an occlusion, such as a chronic total occlusion (CTO) in a lumen of a blood vessel with a medical device to recanalize the vessel. In such instances, it may be possible to recanalize the blood vessel through a subintimal approach using the catheter 10. Turning to FIGS. 8-12, several aspects of an exemplary method for recanalizing an occluded blood vessel using the catheter 10 are illustrated. As shown in FIG. 8, a guidewire 2 may initially be advanced through the lumen 88 of the vessel 80 to a location proximate a proximal end of an occlusion 90 blocking the lumen 88. The guidewire 2 may then be advanced to penetrate outward through the intima layer 82 at a location proximal of the proximal end of the occlusion 90 into the vessel wall 80. With the tip of the guidewire 2 located between the intima layer 82 and the adventitia layer 86, the guidewire 2 may be further advanced distally in a subintimal manner to create a subintimal space between the intima layer 82 and the adventitia layer 86. As shown in FIG. 9, the guidewire 2 may be advanced in a subintimal manner until the distal tip of the guidewire 2 is located distal of the distal end of the occlusion 90 in the subintimal space created, such as by dissection of the tissue layers of the vessel wall 80. In some instances another catheter device may be initially used to exit the lumen 88 proximal of the occlusion 90 and form a subintimal space. In such an instance, the guidewire 2 may be subsequently advanced through the catheter into the subintimal space and the catheter may be withdrawn, leaving the guidewire positioned in the subintimal space as shown in FIG. 9.

Figure 10:
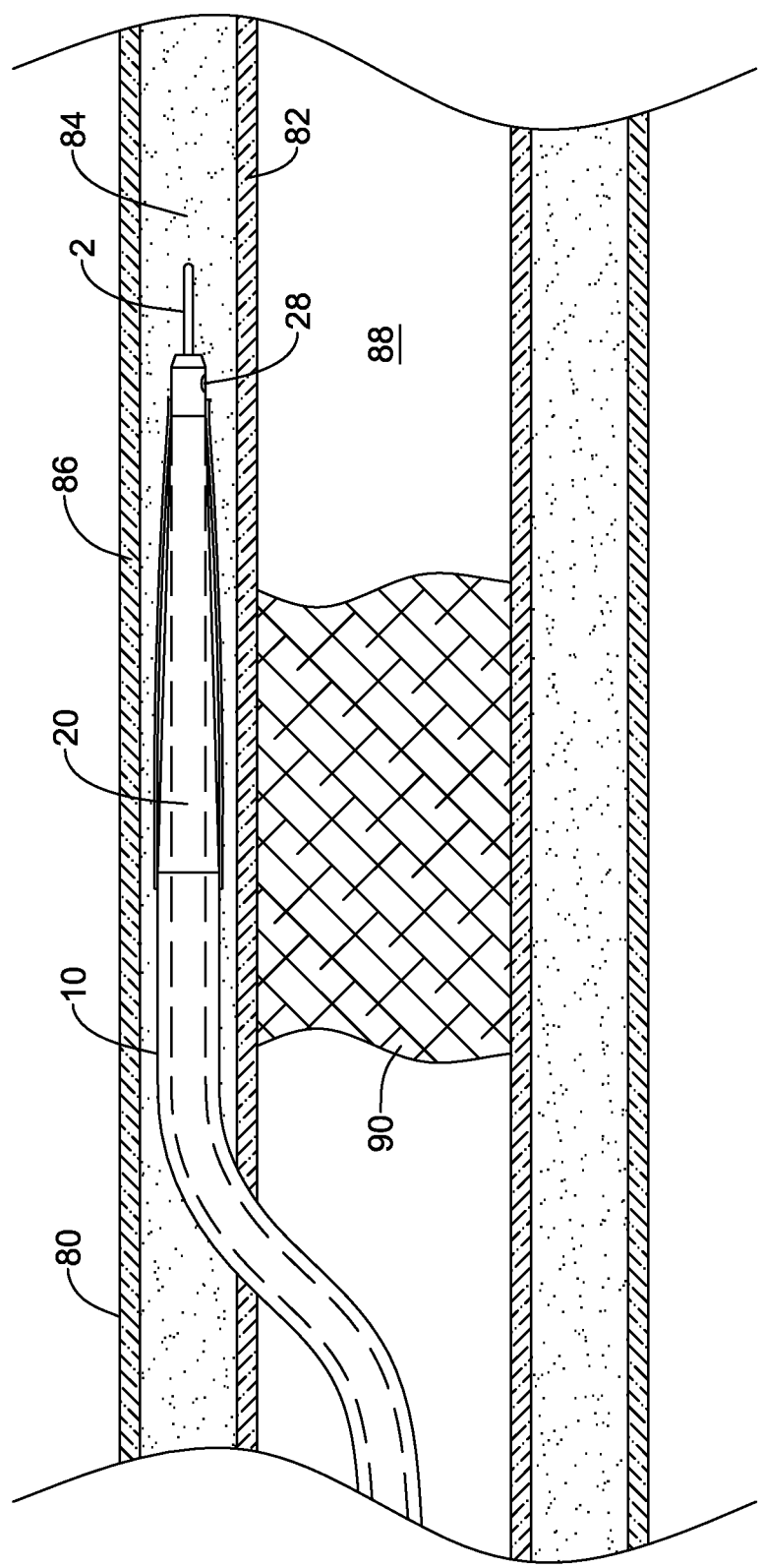

The recanalization catheter 10 may then be advanced distally over the guidewire 2 from the true lumen 88 proximal of the occlusion 90, into the subintimal space between the intima layer 82 and the adventitia layer 86, to a position in the subintimal space in which the distal portion of the catheter 10, including the inflatable balloon 20, is located distal of the distal end of the occlusion 90, as shown in FIG. 10. The recanalization catheter 10 may be advanced through the subintimal space in a delivery configuration, such as with the inflatable balloon 20 in a deflated state. In some instances in which the catheter 10 is configured with a distal tip to facilitate piercing and/or dissection of tissue layers of the blood vessel, a sharp, rigid or piercing feature of the distal tip may be used to pierce and/or dissect tissue layers of the vessel wall 80 as the catheter 10 is advanced distally.

Figure 11:
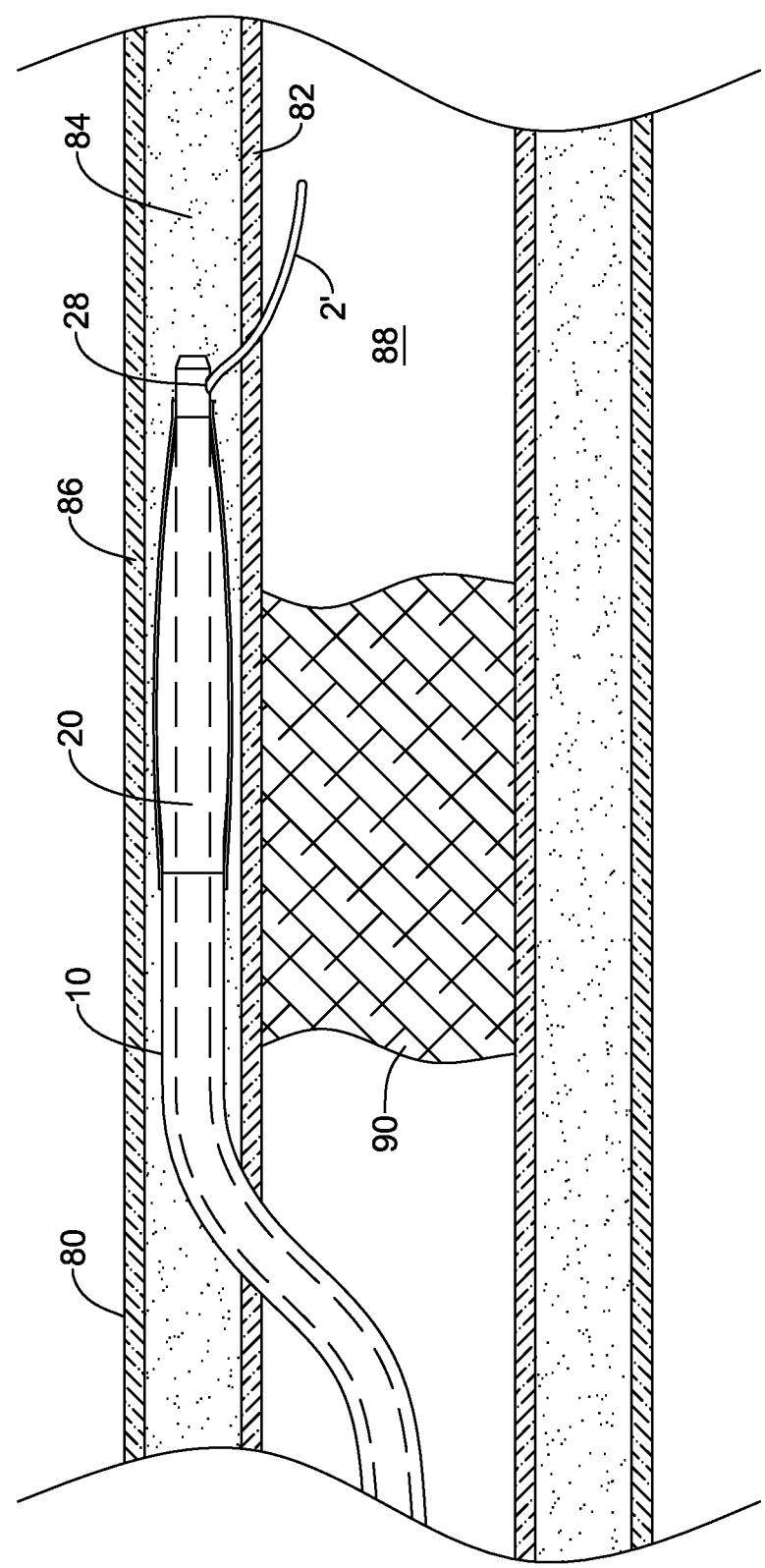

With the lateral port 28 and inflatable balloon 20 positioned distal of the distal end of the occlusion 90, the balloon 20 may be inflated to the first inflation state (i.e., inflated to an inflation pressure less than the threshold inflation pressure) in the subintimal space formed between the intima layer 82 and the adventitia layer 86, as shown in FIG. 11. As the inflatable balloon 20 is inflated to the first inflation state, the third and fourth segments 43, 44 of the balloon 20 may extend laterally away from the catheter shaft 12 in a circumferential orientation within the subintimal space formed in the vessel wall 80 to automatically orient one of the first segment 41 and the second segment 42 of the balloon 20 radially inward toward the true lumen 88 of the blood vessel. Accordingly, inflation of the balloon 20 to the first inflation state will automatically, but arbitrarily orient the lateral port 28 either radially inward toward the true lumen 88 of the blood vessel or radially outward away from the true lumen 88 of the blood vessel. Determination of the orientation of the lateral port 28 may be confirmed by thereafter observing a penetration member exiting the lateral port 28 using fluoroscopy or other imaging technique, for example. In other instances, radiopaque markers, ultrasound or other structures and/or techniques may be used to confirm the orientation of the lateral port 28. In instances in which the lateral port 28 is initially oriented away from the true lumen 88, the balloon 20 may be deflated, the catheter shaft 12 may then be rotated (e.g., rotated about 180°), and the balloon may be reinflated to the first inflation state to orient the lateral port 28 toward the true lumen 88. In some embodiments, the catheter 10 may include two lateral ports 28 positioned on opposite sides of the catheter shaft 12, with a first lateral port 28 arranged with the first segment 41 of the balloon 20 and a second lateral port 28 arranged with the second segment 42 of the balloon 20, thus avoiding a need to deflate, rotate and reorient the lateral port 28. When the lateral port 28 is correctly oriented and facing the true lumen 88, the first segment 41 of the balloon 20 may be facing toward the true lumen 88, while the second segment 42 of the balloon 20 may be facing away from the true lumen 88.

The guidewire 2 may be withdrawn from the guidewire lumen 24, and an elongate penetration member 2' may then be advanced through the guidewire lumen 24, or other device delivery lumen, of the catheter 10 and exit the lateral port 28 to penetrate through the intima layer 82 into the true lumen 88 distal of the occlusion 90, shown in FIG. 11. In some embodiments, the penetration member 2' may be the guidewire 2, or another guidewire introduced through the guidewire lumen 24 of the catheter shaft 12. In other embodiments, the penetration member 2' may be an elongate member, such as a needle cannula or stylet, having a sharpened distal tip configured to pierce through the intima layer 82 into the lumen 88 distal of the occlusion 90. In some instances, the penetration member 2' may include a curved or angled distal tip permitting the penetration member 2' to advance out through the lateral port 28 when the distal tip encounters the lateral port 28. In other instances, the recanalization catheter 10 may include a deflection mechanism to deflect the penetration member 2' out through the lateral port 28.

After achieving re-entry into the true lumen 88 with the penetration member 2', the balloon 20 of the catheter 10 may subsequently be used in a therapeutic procedure. For example, the balloon 20 may then be used to perform angioplasty, stent placement, or pre-dilatation of the blood vessel, for example in the subintimal space formed between the intima layer 82 and the adventitia layer 86 of the vessel wall 80. For example, the inflatable balloon 20 may be subsequently inflated to the second inflation state by inflating the balloon 20 to an inflation pressure above the threshold inflation pressure to perform angioplasty, stent placement, or pre-dilatation of the blood vessel.

In some instances, the balloon 20 may be inflated to the second inflation state without withdrawing the catheter 10 and balloon 20 from the vasculature. In other instances, the catheter 10 and balloon 20 may be withdrawn from the vasculature and then reintroduced into the vasculature to perform angioplasty, stent placement, or pre-dilatation of the blood vessel. For example, in the event the penetration member 2' is a guidewire, the catheter 10 may be withdrawn while leaving the guidewire routed around the occlusion 90 via the subintimal pathway. In instances in which the penetration member 2' is a separate elongate member, such as a needle cannula or stylet, the penetration member 2' may be withdrawn and replaced with a guidewire. The catheter 10 and/or penetration member 2' may be withdrawn while leaving the guidewire routed around the occlusion 90 via the subintimal pathway. The catheter 10 may then be reintroduced into the vasculature by routing the catheter 10 over the guidewire with the guidewire passing through the guidewire lumen 24 from the distal opening 26 of the catheter 10. In instances in which the catheter 10 is subsequently used to place a stent in the vasculature, a stent may be loaded onto the balloon 20 after being withdrawn from the patient.

Figure 12:
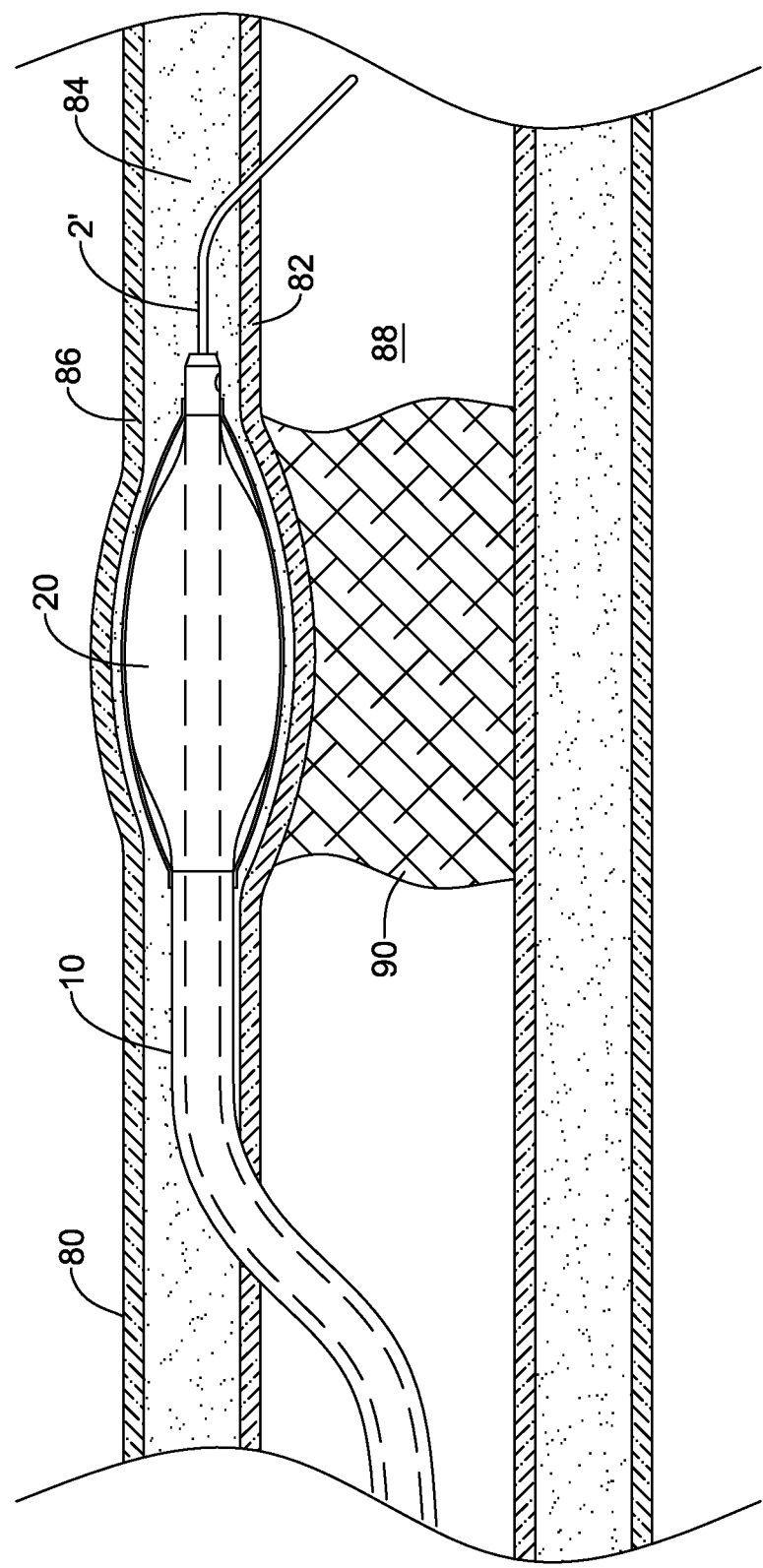

The catheter 10 may be positioned in the vasculature with the balloon 20 positioned at a target location for therapeutic treatment, such as in the subintimal space adjacent the occlusion 90 as shown in FIG. 12. The balloon 20 may be inflated to an inflation pressure greater than the threshold inflation pressure such that the balloon 20 is inflated to the second inflation state, shown in FIG. 12. Inflating the balloon 20 to the second inflation state may deploy a stent in the vasculature, such as in the subintimal space adjacent the occlusion 90 and/or dilate or enlarge the subintimal pathway around the occlusion 90.

Once a pathway has been created across the occlusion 90, (e.g., around the occlusion 90 via a subintimal track), one or more additional medical devices may be advanced through the blood vessel 80 to enlarge the pathway and/or pass distally of the occlusion 90 to perform a further medical procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A recanalization catheter for facilitating re-entry into a lumen of a blood vessel from a subintimal space, comprising:
   an inflatable balloon having a deflated state, a first inflation state, and a second inflation state having a different cross-sectional profile from the first inflation state, wherein in the first inflation state the inflatable balloon has a flattened cross-sectional profile, and in the second inflation state the inflatable balloon has a circular cross-sectional profile; and
   an elongate shaft extending distally from a hub assembly along a longitudinal axis to the inflatable balloon, the elongate shaft including:
      a guidewire lumen having a proximal opening, a distal opening, and a lateral opening in a distal region of the elongate shaft proximal of the distal opening; and
      an inflation lumen in fluid communication with the inflatable balloon;
   wherein the inflatable balloon is configured to be inflated in the subintimal space from the deflated state to the first inflation state at inflation pressures below a threshold inflation pressure and inflated to the second inflation state at inflation pressures above the threshold inflation pressure; and
   wherein the inflatable balloon is configured to orient the lateral opening toward the lumen of the blood vessel when the inflatable balloon is inflated to the first inflation state;
   wherein the inflatable balloon includes a first segment configured to be oriented radially toward the lumen of the blood vessel from the longitudinal axis in the first inflation state, a second segment configured to be oriented radially away from the lumen of the blood vessel from the longitudinal axis, and third and fourth segments interposed between the first and second segments;

wherein in the first inflation state the third and fourth segments are located further from the longitudinal axis than the first and second segments;

wherein, in the first inflation state, the first and second segments are affixed to a guidewire tube of the elongate shaft extending through the inflatable balloon at one or more attachment points; and wherein, in the second inflation state, the one or more attachment points are broken such that the first and second segments are detached from the guidewire tube of the elongate shaft extending through the inflatable balloon.

2. The recanalization catheter of claim 1, wherein in the second inflation state the first, second, third and fourth segments are located about equidistantly from the longitudinal axis.

3. The recanalization catheter of claim 1, wherein the third and fourth segments are configured to have a first radius of curvature in the first inflation state and a second radius of curvature greater than the first radius of curvature in the second inflation state when the inflatable balloon is inflated to an inflation pressure above the threshold inflation pressure.

4. The recanalization catheter of claim 3, wherein the first and second segments are configured to have a first radius of curvature in the first inflation state and a second radius of curvature less than the first radius of curvature in the second inflation state when the inflatable balloon is inflated to an inflation pressure above the threshold inflation pressure.

5. The recanalization catheter of claim 1, wherein the one or more attachment points is an adhesive bond between an interior surface of the first and second segments and the guidewire tube, and wherein the adhesive bond is broken to detach the first and second segments from the guidewire tube when the inflatable balloon is inflated from the first inflation state to the second inflation state.

6. The recanalization catheter of claim 1, wherein the inflatable balloon has an oval cross-section in the flattened cross-sectional profile.

7. A recanalization catheter for facilitating re-entry into a lumen of a blood vessel from a subintimal space, comprising:

an elongate shaft extending distally from a hub assembly;

an inflatable balloon mounted on a distal region of the elongate shaft, the inflatable balloon configured to be inflated in the subintimal space from a deflated state to a first inflation state at inflation pressures below a threshold inflation pressure and inflated to a second inflation state at inflation pressures above the threshold inflation pressure, wherein in the first inflation state the inflatable balloon has a flattened cross-sectional profile and in the second inflation state the inflatable balloon has a circular cross-sectional profile; and means for retaining the inflatable balloon in the first inflation state until the inflatable balloon is inflated to an inflation pressure above the threshold inflation pressure.

8. The recanalization catheter of claim 7, wherein the means for retaining the inflatable balloon in the first inflation state comprises:

first and second bonding portions on an interior surface of the inflatable balloon being bonded to a guidewire tube of the elongate shaft extending through the inflatable balloon in the first inflation state;

wherein the first and second bonding portions are configured to be unbonded from the guidewire tube when the inflatable balloon is inflated to an inflation pressure above the threshold inflation pressure.

9. The recanalization catheter of claim 7, wherein the means for retaining the inflatable balloon in the first inflation state comprises: one or more interior struts extending between the balloon and a guidewire tube of the elongate shaft extending through the inflatable balloon in the first inflation state; wherein the one or more interior struts are configured to be broken from the guidewire tube and/or the inflatable balloon when the inflatable balloon is inflated to an inflation pressure above the threshold inflation pressure.

10. The recanalization catheter of claim 7, wherein the means for retaining the inflatable balloon in the first inflation state comprises:

first and second curved segments of the inflatable balloon having a first thickness; and third and fourth curved segments of the inflatable balloon interposed between the first and second curved segments, the third and fourth curved segments having a second thickness greater than the first and second curved segments;

wherein the third and fourth curved segments are configured to have a first radius of curvature in the first inflation state and a second radius of curvature greater than the first radius of curvature in the second inflation state when the inflatable balloon is inflated to an inflation pressure above the threshold inflation pressure.

11. The recanalization catheter of claim 7, wherein the means for retaining the inflatable balloon in the first inflatable state comprises:

first and second curved segments of the inflatable balloon having a first stiffness; and third and fourth curved segments of the inflatable balloon interposed between the first and second curved segments, the third and fourth curved segments having a second stiffness different than the first and second curved segments;

wherein the third and fourth curved segments are configured to have a first radius of curvature in the first inflation state and a second radius of curvature greater than the first radius of curvature in the second inflation state when the inflatable balloon is inflated to an inflation pressure above the threshold inflation pressure.

12. The recanalization catheter of claim 7, wherein the means for retaining the inflatable balloon in the first inflation state comprises:

a first longitudinal stiffening member extending along the inflatable balloon; and a second longitudinal stiffening member extending along the inflatable balloon opposite the first longitudinal stiffening member;

wherein the first and second longitudinal stiffening members are configured to elastically yield when the inflatable balloon is inflated to an inflation pressure above the threshold inflation pressure.

13. The recanalization catheter of claim 7, wherein the threshold inflation pressure is in the range of about 4-6 ATM.

14. The recanalization catheter of claim 7, wherein the inflatable balloon is in the first inflation state at inflation pressures between 2-4 ATM.

15. The recanalization catheter of claim 14, where the inflatable balloon is in the second inflation state at inflation pressures greater than 6 ATM.

16. A method of recanalizing a blood vessel having an occlusion therein, the method comprising:

advancing a distal region of a catheter shaft including an inflatable balloon mounted thereon into a subintimal space between a first tissue layer and a second tissue layer of a wall of a blood vessel, the inflatable balloon having a deflated state, a first inflation state, and a second inflation state having a different cross-sectional profile from the first inflation state, wherein in the first inflation state the inflatable balloon has a flattened cross-sectional profile, and in the second inflation state the inflatable balloon has a circular cross-sectional profile;

inflating the inflatable balloon from the deflated state to the first inflation state in the subintimal space by inflating the inflatable balloon to a first inflation pressure below a threshold inflation pressure to orient a lateral port in the distal region of the catheter shaft toward a lumen of the blood vessel distal of the occlusion;

advancing a penetration member from the lateral port of the catheter shaft to penetrate through the first tissue layer into the lumen of the blood vessel; and thereafter, inflating the inflatable balloon to the second inflation state different from the first inflation state by inflating the inflatable balloon to a second inflation pressure above the threshold inflation pressure to expand the subintimal space.

17. The method of claim 16, wherein inflating the inflatable balloon to the second inflation state causes first and second segments of the inflatable balloon to be detached from a guidewire tube of the catheter shaft extending through the inflatable balloon when the inflatable balloon is inflated to the second inflation pressure above the threshold inflation pressure.

18. The method of claim 16, wherein the inflatable balloon has an oval cross-section in the flattened cross-sectional profile.

19. The method of claim 16, wherein inflating the balloon from the first inflation state to the second inflation state breaks one or more adhesive bonds between the inflatable balloon and the catheter shaft.

* * * * *